US012766079B2

(12) United States Patent
Becker et al.

(10) Patent No.: US 12,766,079 B2
(45) Date of Patent: Oct. 20, 2026

(54) METHODS OF FORMING DRY-TO-THE-TOUCH PEROXIDE COMPOSITIONS

(71) Applicant: ARKEMA INC., King of Prussia, PA (US)

(72) Inventors: Christian G. Becker, King of Prussia, PA (US); Jay F. Miller, King of Prussia, PA (US); John M. Richardon, King of Prussia, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 18/722,576

(22) PCT Filed: Nov. 11, 2022

(86) PCT No.: PCT/US2022/049649
§ 371 (c)(1),
(2) Date: Jun. 20, 2024

(87) PCT Pub. No.: WO2023/121786
PCT Pub. Date: Jun. 29, 2023

(65) Prior Publication Data

US 2025/0064694 A1 Feb. 27, 2025

Related U.S. Application Data

(60) Provisional application No. 63/292,624, filed on Dec. 22, 2021.

(51) Int. Cl.

| | |
|---|---|
| ***A61K 8/22*** | (2006.01) |
| ***A01N 25/12*** | (2006.01) |
| ***A01N 59/00*** | (2006.01) |
| ***A01P 1/00*** | (2006.01) |
| ***A61K 8/25*** | (2006.01) |
| ***A61Q 19/00*** | (2006.01) |
| ***B01J 2/06*** | (2006.01) |

(52) U.S. Cl.
CPC ................ *A61K 8/22* (2013.01); *A01N 25/12* (2013.01); *A01N 59/00* (2013.01); *A01P 1/00* (2021.08); *A61K 8/25* (2013.01); *A61Q 19/00* (2013.01); *B01J 2/06* (2013.01); *A61K 2800/10* (2013.01)

(58) Field of Classification Search
CPC .................................. A61K 8/22; A61K 8/25
See application file for complete search history.

(56) References Cited

U.S. PATENT DOCUMENTS

| | | | |
|---|---|---|---|
| 8,485,139 B2 | 7/2013 | Kim et al. | |
| 2006/0278847 A1 | 12/2006 | Walzer et al. | |
| 2007/0055009 A1 | 3/2007 | Hasenzahl et al. | |
| 2009/0252815 A1 | 10/2009 | Walzer et al. | |
| 2011/0190191 A1* | 8/2011 | Balgobind-Narain ...................... | C11D 3/505 427/212 |
| 2014/0227333 A1* | 8/2014 | Smith ................. | C11D 3/3947 252/186.25 |
| 2020/0299621 A1* | 9/2020 | Becker ............... | C11D 17/0034 |

FOREIGN PATENT DOCUMENTS

| | | |
|---|---|---|
| GB | 2169308 A | 7/1986 |
| JP | 5014864 B2 | 8/2012 |
| JP | 2020535285 A | 12/2020 |
| KR | 101245548 B1 | 3/2013 |
| WO | 2014126831 A1 | 8/2014 |

OTHER PUBLICATIONS

International Search Report (PCT/ISA/210) with English translation mailed on Mar. 6, 2023, by the Commissioner for Patents as the Internal Searching Authority for International Application No. PCT/US2022/049649.
Notice of Reasons for Refusal dated Sep. 1, 2026, issued by the Japanese Patent Office in Japanese Patent Application No. 2024-538288. 4 Pages.
Elsevier Powder Technology 189 (2009) 263-269. "Influence of Mixing Characteristics for Water Encapsulation by Self-Assembling Hydrophobic Silica Nanoparticles". Laurent Forney et al.

* cited by examiner

*Primary Examiner* — Austin Murata
(74) *Attorney, Agent, or Firm* — Debodhonyaa Sengupta

(57) ABSTRACT

Methods of blending liquid peroxide solutions and crystalline or amorphous solid materials to provide a dry-to-the-touch peroxide containing solid materials.

19 Claims, No Drawings

METHODS OF FORMING DRY-TO-THE-TOUCH PEROXIDE COMPOSITIONS

FIELD OF THE INVENTION

The present invention pertains to methods of blending of peroxide solutions and crystalline or amorphous solid materials to provide a dry-to-the-touch peroxide containing powder materials.

BACKGROUND OF THE INVENTION

Liquid peroxides and solutions of peroxide compounds are useful for many applications from industrial sources of oxidizers and free radicals to cosmetics and household sanitizers, but because they generally are liquid, unstable and reactive, convenient storage and delivery has long been a challenge.

A solid form of a peroxide compounds that could take the form of a dry powder, pellet, tablet, bead, or brick, having long term stability, have a broad range of applications: formulations for personal care, cosmetic, agriculture, and health care applications, to mention only a few. U.S. Patent publication No. 2020/0299621, incorporated herein by reference, discloses a delivery system for one peroxide compounds that uses an inorganic solid support that is inert to the peroxide compound and is capable of adsorbing a considerable quantity of liquid while remaining dry-to-the-touch.

SUMMARY OF THE INVENTION

The novel concepts presented in the present invention relate to methods to incorporate peroxide compounds such as hydrogen peroxide into solid supports to provide a dry-to-the-touch peroxide containing powder. The mixtures are completely dry-to-the-touch and the liquid does not seep out or otherwise cause the final powders to feel damp or wet even after long periods of storage. The liquid peroxide component of the present invention can comprise hydrogen peroxide, peracetic acid, organic peroxide, or combinations of various peroxides or other aqueous based peroxide products. The liquid peroxide component can also include additives such as stabilizers. The liquid peroxide component is incorporated into a solid support so as to form a dry-to-the-touch powder that incorporates the peroxide material. The solid support can be a base of fumed or pyrogenic silica, precipitated silica or combination in different ratios of both types of silica, either hydrophobic or hydrophilic in order to achieve the desired carrier properties. Other solids could also be incorporated into the silica base such as blending agents, coloring agents, binding agents to provide desirable aspects to the end product such as product color.

The peroxide components can be incorporated into the solid support component via a variety of methods to achieve proper blending. Such blending methods include a simple mixed tank with the liquid introduced by way of one or more nozzles, fogging devices, spray balls, or dripping method using a ribbon or paddle blender, screw blender, rotating plough blender, plow blender, double paddle blender, tumbling blender, V-cone blender, double cone blender, static blender, drum blender, planetary blender, vertical blender, homogenizer, or similar equipment allowing a thorough mixing of the powder component and the liquid peroxide component. It is also possible to spray the liquid peroxide solution into a fluidized bed. The spray nozzles may be flat spray nozzles, cone spray nozzles, hollow cone spray nozzles, or mist/fog nozzles. Other mixing technologies can be employed as well, such as vibration-assisted mixing equipment, sonic or ultrasound mixing, and various shakers. Many types of solid/liquid mixing equipment exist. For the purposes of the present invention, the terms mixer/mixing and bender/blending can be used interchangeably in describing the incorporation of the peroxide components into the solid support.

In preparing the solid peroxide material, it is important that an appropriate amount of shear be applied to the powder solid support to form a uniform product. Simply mixing the liquid into the solid, for example, will in general not provide sufficient shear and will tend to result in silica support particles that tend to stick together and agglomerate. While providing sufficient shear to provide a uniform product, it is also important that the blending operation not overly shear the solid support material.

The blending operation used to form the solid peroxide product must be controlled so as to maintain the integrity of the support, typically silica, microstructure. Having excessive shear will quickly and irreversibly destroy the physical structure of the silica support. Applying too much shear to the product creates a partial to complete breakdown of the silica support structure and leads to non-usable wet, mushy product.

Typically, when spraying a liquid onto solid particles, the operation should be done in a regime of a Froude number (Fr) greater than 1. If Fr is less than 1, the gravity forces will be stronger than the centrifugal forces, the solid particles will remain settled in the blender, moved, but not in a cloud. If Fr is greater than 1, the centrifugal forces will tend to be stronger than the gravity force and the solid particles will have a tendency to be lifted and suspended in the blender. However, operating with solid particles that have a very low bulk density causes the solid particles to become air borne, some of which is lost to a filter or air.

In order to ensure the integrity of the solid peroxide product, a blender must be operated under conditions of low shear. Doing so requires operation of the blender under conditions of a low Froude number. However, when performing liquid injection onto a solid, it is typical that a Froude number greater than 1 be employed. In the present invention, using a high mixing speed may cause the silica to lose its microstructure. The present inventors have surprisingly found that when operating a blender under conditions with a Froude number less than one, the rate of liquid injection must be reduced, to allow time for the proper distribution of the liquid.

Defining the mixing time ($t_m$) as the ratio of the volume of the solid powder to the liquid feed flow rate operating at a $t_m$ between 5 and 45 minutes, preferably 10 to 35 minutes, and more preferably 15 to 30 minutes allows operation at a low Froude number to reduce shear on the solid particles, yet still allow full and uniform incorporation of the solid particles by the liquid.

When using too little shear to incorporate the liquid peroxide solution into the solid particles, silica support, some of the solid particles will agglomerate forming a ball that not only feels wet to the touch, like a wet snowball, but also contains a high concentration of peroxide solution. The present invention reduces or eliminates the formation of agglomerates and produces a uniform powder that is dry-to-the-touch and has uniform hydrogen peroxide distribution throughout the solid support.

DETAILED DESCRIPTION OF CERTAIN EMBODIMENTS OF THE INVENTION

The present inventors have discovered that when blending a solution of liquid peroxide into a silica powder support, particular attention must be made to ensure that the silica is appropriately blended to reduce the number of unwanted agglomerates in the final product. Some agglomerates are typically already present in the silica component. They can form during packaging and shipping. Other agglomerates can appear when the silica particles are wetted with the addition of the liquid peroxide solution causing inhomogeneous particle-particle adhesion. The present invention provides processes whereby the silica support is wetted with the peroxide solution such that the distribution of peroxide throughout the silica is relatively uniform. The resulting wetted silica has no agglomerates or only a few agglomerates after the blending process is completed. A solid peroxide product is formed by the process of the present invention, which provides for minimal agglomerates in the silicate, proper wetting of the silica to avoid clumping and uniformity of the wetting process. The solid peroxide product formed by the process of the present invention is a dry-to-the-touch powder.

A preferred method of blending the liquid peroxide component and the solid, silica support component is the use of a double blade ribbon blender, paddle blender or plough blender. A preferred method is to operate the blender of a ribbon, double ribbon or paddle blender at a blade tip speed preferably between about 0.5 and about 10.0 m/s, preferably 1.0 m/s to about 5.0 m/s and more preferably between about 0.5 and about 2.5 m/s while delivering the peroxide solution to the silica support component with spray nozzles. Alternative types of blenders may operate at different tip speeds to achieve the desired mixing. When the desired amount of peroxide solution has been added to the silica support, the impellors are preferably continued to operate at the same blade tip speed to reduce the amount of clumping and to ultimately produce a solid silica product (containing the liquid peroxide) that is a powder substantially dry-to-the-touch. A feature of the present invention is to provide sufficient shear for good distribution of the silica support powder but not so much shear so as to negatively impact the silica structure. "Dry-to-the-touch" is established to mean that a 1 ply AccuWipe® brand #29712 by Georgia-Pacific absorbs less than 15% moisture by weight after being immersed in the product peroxide containing powder for 24 hours at 25 degrees C.

Along with the impeller tip speed, the Froude number is an important parameter to consider in regards to the present invention. The Froude number is defined as the ratio of the centrifugal to gravitational forces:

$$Fr = R\omega^2/g$$

where R is the radius of the blender ω is the angular velocity and g is the gravity. If the Fr number is greater than 1, the centrifugal forces dominate, i.e., the powder is thrown around in the blender and the powder will have a tendency to be lifted and suspended in air in the blender. Typical operation of spraying liquids onto a solid are performed at Fr greater than 1. However, when employing very light, fluffy solid silica support, the air becomes full of powder causing excess losses to the filters (or atmosphere) and powder getting onto and into the liquid nozzles. In the present invention, the/blender is operated at a Fr equal to or less than 1 and more than 0.05, preferably less than 0.7 and more than 0.075, and more preferably less than 0.5 and more than 0.1.

The present inventors have surprisingly found that good product can be produced at low Fr. With appropriate geometry and flow from the nozzles, production of a dry-to-the-touch powder with minimal or no agglomerate formation is produced. The blending time, $t_m$, is defined as the ratio of the volume of product in the blending vessel to the flow rate of the liquid $$t_m = \text{Vol. powder in blender}/Q \text{ where}$$

Q is the volumetric flow rate.

In accordance with the present invention, the blender is operated with $t_m$ between than 5 and 45 minutes, preferably 10 to 35 minutes, and more preferably 15 to 30 minutes. This allows operation at a low Froude number to reduce shear on the powder, yet still allows full and uniform coverage of the solid silica support powder with the peroxy liquid.

The location of the spray nozzle or nozzles and the nozzle spray geometry are aligned in such a way that the spray from the nozzles does not hit the blending unit walls or other fixtures located within the blending unit during the blending process. Spray hitting the blending unit wall or any solid fixture within the blending unit can create wet spots that lead to the formation of unwanted agglomerates. Multi-nozzle configurations and geometries can be employed that avoid spray patterns that hit the blending unit walls or internal equipment or that overlap. Spray pattern overlap creates localized spatial wet spots that lead to undesirable agglomerates. The spraying of the liquid peroxide component is designed under the operating pressure conditions for the type of nozzle and with nozzle alignment to generate a uniform distribution of droplets within the blending unit while minimizing wet spots. Spraying of small droplets is preferred but it is also possible in some conditions to use nozzles that create fine or ultra-fine droplets of liquid leading to a fog or mist type of spray.

In addition to spray pattern, another feature of the present invention is the spray droplet sizes. Spray nozzles are used to distribute liquid and create droplets with high surface area, which droplets impact on solid surfaces. In the present invention, the spray device is used to distribute the peroxide liquid component with controlled droplet velocity. In the present invention, very high droplet velocity especially when coupled with large droplets is not desired as it can result in the formation of larger agglomerates. In the present invention, it is preferable to spray droplets with small diameters and have nozzles with low flow rates. It was discovered that in the formation of the dry peroxide composition, it is not possible to linearly increase the flow rate in order to increase productivity. It was discovered that in order to scale up, it is necessary to increase the number of spray nozzles to increase the flow rate of the peroxide component to maintain an even distribution with little overlap or spray hitting the walls or other fixtures located within the blending unit during the blending process. The present inventors found that the ratio of the liquid peroxide component spray droplet size to the silica support particle size is preferably between 0.5 and 10,000, and more preferably between 0.75 and 3,000. For example, with silica of 0.2 to 0.3 microns, the liquid peroxide component spray droplet size would be between 0.1 and 300 microns.

A preferred spray nozzle for the liquid peroxide component would have a flow below about 1 gpm (3.78 liters per minute) and preferably less than 0.5 gpm (1.89 liters per minute) at 40 psig (276 kPa) for a small 75 liters blending unit. A preferred droplet size distribution provided for reference (not a limiting factor to this process) would be from 0.1 to 3,000 microns, and preferably 1 to 1,000 microns, and more preferably 5 to 800 microns. Various spray patterns (flat spray, cone, hollow cone, etc.) can be used. The selection of the spray pattern is a function of the size and geometry of the blending unit. The viscosity of the liquid peroxide component will also influence the flow rate and spray pattern selection to provide the features of the present invention.

The present inventors discovered that to provide a solid peroxide product with controlled formation of agglomerates the ratio between the related blending unit size (and related shear) and the flow rate at which the peroxide liquid component is added must be controlled. The ratio for a single nozzle preferably ranges from about 0.01 to about 1.5 liters, more preferably from about 0.05 to about 0.5 liter of liquid peroxide component sprayed per minute per nozzle per 100 L of blending unit space (working volume). Accordingly, for example, a blending unit of 1273 liters would require between 2 and 6 nozzles flowing at about 1.5 liters per minute to provide the proper addition of the liquid peroxide component to the powder silica component at the correct ratio in order to limit the formation of agglomerates.

To enhance safety in handling of the liquid peroxide component such as hydrogen peroxide and peracetic acid, it is preferred to operate the blending unit at ambient temperature ranging from about 4° C. to 35° C., and preferably from about 10° C. to 30° C. and more preferably from about 15° C. to 25° C. in vented conditions. The metal parts in contact with the peroxide should be passivated to ensure the stability of the product.

Aspect 1: A method of preparing a combination of liquid peroxide and dry solid support comprising spraying a liquid peroxide solution onto a dry silica solid support comprising mixing a hydrophobic or hydrophilic silica powder in a blending unit comprising mixing apparatus and one or more spray nozzles to form a powder relatively free of any agglomeration wherein the spray nozzles are oriented to minimize impact of the spray on the surfaces of the blending unit or mixing apparatus and the ratio of the liquid peroxide spray droplet size to the silica solid support particle size is between about 0.5 and 10,000 and the blending unit is operated at a Froude number of 1 or less.

Aspect 2: The method of aspect 1, wherein the flow rate of liquid peroxide solution comprises an aqueous solution.

Aspect 3: The method of aspects 1 or 2 wherein the liquid peroxide solution comprises aqueous hydrogen peroxide, peracetic acid, organic peroxide or combination thereof.

Aspect 4: The method of any of aspects 1 to 3 wherein the concentration of the liquid peroxide solution is from about 0.5% to 90% and preferably, 35% to 70 and more preferably 50 to 70%.

Aspect 5: The method of any of aspects 1 to 4, wherein the silica support comprises fumed silica, pyrogenic silica, precipitated silica or combinations thereof.

Aspect 6: The method of any of aspects 1 to 5, wherein the silica support is in the form of a powder or granules.

Aspect 7: The method of any of aspects 1 to 6, wherein the mixing apparatus comprises a blender operated at a blade tip speed between about 0.5 m/s and about 10.0 m/s.

Aspect 8: The method of any of aspects 1 to 7, wherein the ratio of the liquid peroxide spray droplet size to the silica solid support particle size is between about 0.5 and 10000, and preferably between about 0.75 and 3,000.

Aspect 9: The method of any of aspects 1 to 8, wherein the liquid peroxide component flow rate through each one of the one or more nozzles ranges from about 0.3 gpm (1.13 liter per minute) to about 2 gpm (7.57 liters per minute) at 40 psig (276 kPa).

Aspect 10: The method of any of aspect 1 to 9, wherein the one or more spay nozzles are selected from the group consisting of flat spray nozzles, cone spray nozzles, hollow cone spray nozzles, mist/fog nozzles and combinations thereof.

Aspect 11: The method of any aspect 1 to 10, wherein the blender is run at a Froude number less than 1 and more than 0.05, preferably less than 0.7 and greater than 0.075, and more preferably less than 0.5 and more than 0.1.

Aspect 12: The method of any aspect 1 to 11, wherein the spray delivery system is run with a mixing time between than 5 and 45, preferably 10 to 35, and more preferably 15 to 30 minutes.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the composition or the method for using the composition. Additionally, in some embodiments, the invention can be construed as excluding any element or process step not specified herein.

EXAMPLES

Example 1

A 75 L double ribbon blender was operated at speed of 60 RPM. A Bete PJ24 90° spray angle nozzle working at high pressure (100 psig or 689 kPa) provided 50% liquid hydrogen peroxide solution at 0.16 gpm (0.60 liter per minute) into 2.5 kg Cab-O-Sil® M5 silica to make 8.6 kg product. The spray pattern resulted in spray hitting the blending unit wall. The resulting product contained a large number of agglomerates, and was wet-to-the-touch and had a "snowball" type texture.

Example 2

In the same 75 L double ribbon blending unit, a Teejet® nozzle, which provided a flat spray pattern, was used with a 50% liquid hydrogen peroxide solution component flow rate of 0.2 gpm (0.76 liter per minute) at 40 psig (276 kPa) into 2.5 kg Cab-O-Sil® M5 silica to make 8.6 kg product. The product quality improved but there was still some wet agglomerate formation.

Example 3

In the same 75 L double ribbon blending unit, a Teejet® nozzle, which provided a flat spray nozzle with a flow rate of about 0.067 gpm (0.25 liter per minute) at a pressure under 40 psig (276 kPa) into 2.5 kg Cab-O-Sil® M5 silica led a total of 8.6 kg of good quality product, dry-to-the-touch powder, with minimal agglomerate formation.

Example 4

In a commercial size 1273 L paddle blender, 139 pounds (63 kg) of silica (Cab-O-Sil® M5 available from Cabot Corp.) was loaded into the blender which occupied about 90% of the blender volume. The spray nozzles were directly outside of the silica. The blender was operated at a speed of 20.5 RPM, using a series of 5 TeeJet® flat nozzles with a flow of 0.4 gpm (1.5 liter per minute) at a pressure of 30 psig (207 kPa), placed in a way that the spray patterns did not overlap or hit the blender sidewalls. A good quality product, dry-to-the-touch powder, with no agglomerate formation resulted. The Froude number was calculated to be 0.21, which is considerably less than 1 which literature states is ideal for mixing powers and liquid. The tip speed of the paddles was about 1 m/s. The blender was turned on with no discernable notice of dust in the dust collector. The 50.1% hydrogen peroxide addition occurred over 19 minutes and a total of 366 pounds (166 kg) of hydrogen peroxide was added, though it was calculated that 357 pounds (162 kg) actually went into the blender as 9 pounds (4 kg) filled the feed lines. After the hydrogen peroxide was added, the blender was allowed to blend for an additional 5 minutes with the chopper turned on for 5 seconds every minute. The resulting product was a free flowing dry-to-the-touch powder and was analyzed to have 36% hydrogen peroxide incorporated into the silica.

What is claimed is:

1. A method of preparing a combination of liquid peroxide and dry solid support comprising spraying a liquid peroxide solution onto a dry silica solid support comprising mixing a hydrophobic or hydrophilic silica powder in a blending unit comprising mixing apparatus and one or more spray nozzles to form a powder wherein the spray nozzles are oriented to minimize impact of the spray on the surfaces of the blending unit or mixing apparatus and the ratio of the liquid peroxide spray droplet diameter to the silica solid support particle diameter is between about 0.5 and 10,000 and the blending unit is operated at a Froude number of 1 or less.

2. The method of claim 1, wherein the liquid peroxide solution is an aqueous solution.

3. The method of claim 1 wherein the liquid peroxide solution comprises hydrogen peroxide, peracetic acid, organic peroxide or combination thereof.

4. The method of claim 1 wherein the liquid peroxide solution is an aqueous solution having a concentration from about 0.5% to 70% of liquid peroxide in said aqueous solution.

5. The method of claim 1 wherein the liquid peroxide solution is an aqueous solution having a concentration from 35% to 70% of liquid peroxide in said aqueous solution.

6. The method of claim 1 wherein the liquid peroxide solution is an aqueous solution having a concentration from 50% to 70% of liquid peroxide in said aqueous solution.

7. The method of claim 1, wherein the silica solid support comprises fumed, pyrogenic silica or precipitated silica or combinations thereof.

8. The method of claim 1, wherein the silica solid support is in the form of a powder or granules.

9. The method of claim 1, wherein the mixing apparatus comprises a blender operated at a blade tip speed between about 0.5 m/s and about 10.0 m/s.

10. The method of claim 1, wherein the ratio of the liquid peroxide spray droplet size to the silica solid support particle size is between about 0.5 and 10,000.

11. The method of claim 1, wherein the ratio of the liquid peroxide spray droplet size to the silica solid support particle size is between about 0.75 and 3,000.

12. The method of claim 1, wherein the flow rate of the liquid peroxide solution through each one of the one or more nozzles ranges from about 0.5 gpm (1.89 liter per minute) to about 2 gpm (7.57 liters per minute) at 40 psig (276 kPa).

13. The method of claim 1, wherein the one or more spay nozzles are selected from the group consisting of flat spray nozzles, cone spray nozzles, hollow cone spray nozzles, mist/fog nozzles and combinations thereof.

14. The method of claim 1, wherein the blending unit is operated at a Froude number less than 1 and more than 0.05.

15. The method of claim 14, wherein the blending unit is operated at a Froude number less than 0.7 and more than 0.075.

16. The method of claim 14, wherein the blending unit is operated at a Froude number less than 0.5 and more than 0.1.

17. The method of claim 1, wherein the blending unit is operated at a mixing time between 5 and 45 minutes.

18. The method of claim 17, wherein the blending unit is operated at a mixing time between 10 to 35 minutes.

19. The method of claim 17, wherein the blending unit is operated at a mixing time between 15 to 30 minutes.

* * * * *